United States Patent
Kang et al.

(10) Patent No.: US 9,884,086 B2
(45) Date of Patent: Feb. 6, 2018

(54) ADMINISTRATION METHOD FOR ANTICANCER DRUGS

(71) Applicant: Dong-A University Research Foundation for Industry—Academy Cooperation, Busan (KR)

(72) Inventors: Tae Hong Kang, Busan (KR); Jeong Min Park, Gyeongsangnam-do (KR); Ji Ye Choi, Gyeongsangnam-do (KR); Sun Hee Leem, Busan (KR)

(73) Assignee: DONG-A UNIVERSITY RESEARCH FOUNDATION FOR INDUSTRY—ACADEMY COOPERATION, Busan (KR)

( * ) Notice: Subject to any disclaimer, the term of this patent is extended or adjusted under 35 U.S.C. 154(b) by 74 days.

(21) Appl. No.: 14/551,088

(22) Filed: Nov. 24, 2014

(65) Prior Publication Data

US 2015/0290282 A1 Oct. 15, 2015

(30) Foreign Application Priority Data

Apr. 9, 2014 (KR) .......................... 10-2014-0042629

(51) Int. Cl.
*A61K 38/16* (2006.01)
*A61K 31/403* (2006.01)
*A61K 31/7105* (2006.01)
*A61K 33/24* (2006.01)
*A61K 45/06* (2006.01)

(52) U.S. Cl.
CPC ............ *A61K 38/16* (2013.01); *A61K 31/403* (2013.01); *A61K 31/7105* (2013.01); *A61K 33/24* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 9,265,772 | B2* | 2/2016 | Bersot | A61K 31/403 |
| 2008/0220092 | A1* | 9/2008 | Dipierro | A61K 31/135 |
| | | | | 424/649 |
| 2010/0028876 | A1* | 2/2010 | Gordon | G01N 33/57423 |
| | | | | 435/6.11 |
| 2012/0134985 | A1* | 5/2012 | Evans | A61K 31/00 |
| | | | | 424/131.1 |
| 2013/0303524 | A1* | 11/2013 | Bersot | A61K 31/403 |
| | | | | 514/222.5 |

OTHER PUBLICATIONS

Yang et al. Journal of Biological Chemistry 285(5) (2010) 3030-3034.*
Levi, et al. Advanced Drug Delivery Reviews 59 (2007) 1015-1035, 1018.*
Ohdo, S. Advanced Drug Delivery Reviews 62 (2010) 859-875.*
Ohdo, S. Advanced Drug Delivery Reviews 62 (2010) 857-858.*
Piergiovanni et al. Cell Cycle, 9(18) 3686-3690.*
Kang, T.H. and Leem, S.H., Nucleic Acids Res., 42:4427. (Year: 2014).*
Michele A. Gauger, Aziz Sancar. Cryptochrome, Circadian Cycle, Cell Cycle Checkpoints, and Cancer. Cancer Res 2005; 65:6828-34.

* cited by examiner

*Primary Examiner* — Michael Barker
(74) *Attorney, Agent, or Firm* — The PL Law Group, PLLC

(57) ABSTRACT

Disclosed is a method for providing information used for comparing restoration rates of damaged DNA, wherein information about a time period when Ataxia telangiectasia and Rad3 related ('ATR') activation is accelerated, on the basis of alternative information about an expression level of cryptochrome may be acquired, therefore, it can be determined that a restoration rate of damaged DNA is high at a time period when the expression level of cryptochrome is high. Accordingly, a time period when a restoration rate of DNA damaged by different causes is high, can be determined. Further, it is possible to estimate a time period when side effects occurring due to using an anticancer drug are minimized, and then, utilize the estimated result in determining the timing of administration of an anticancer drug.

5 Claims, 11 Drawing Sheets

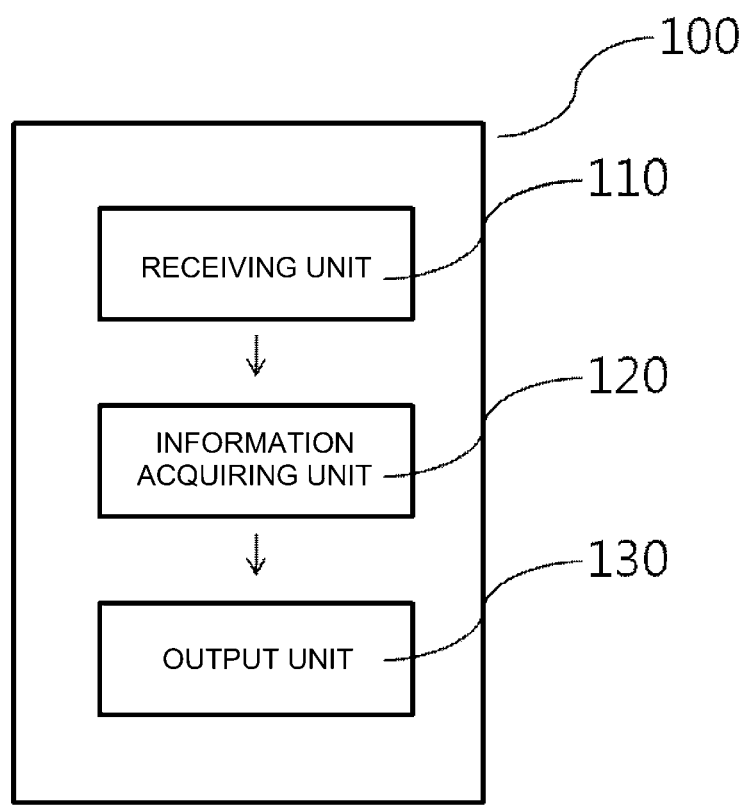

ADMINISTRATION METHOD FOR ANTICANCER DRUGS

CROSS-REFERENCE TO RELATED APPLICATION

This application claims priority from Korean Patent Application No. 10-2014-0042629, filed on Apr. 9, 2014 in the Korean Intellectual Property Office, the entire disclosure of which is incorporated herein by reference.

GOVERNMENT LICENSE RIGHTS

This invention was made with Korean government support under Project No. 1345204187 (Research Program: Leading researcher) support awarded by Department of Ministry of Science, ICT and Future Planning (Research management institution: National Research Foundation of Korea) for the Research subject of Optimal Development of cancer treatment through a study on the biological, physical characteristics of cancer. The Korean government has certain rights in the invention.

BACKGROUND

1. Field of the Invention

The present invention relates to an administration method of anticancer drugs.

2. Description of the Related Art

Substantially all living things on earth exhibit one common cyclicalbiological rhythm, known as a 'circadian rhythm,' with a period of 24 hours in order to adapt themselves to a change of day and night resulting from the rotation of the earth. More particularly, such a circadian rhythm involves a behavioral rhythm of being active during the daytime while sleeping at night, a physiological rhythm including, for example, hormone secretion with repeated rises and falls over a period of one day, variation of body temperature, expression of genes, etc., and the like, which are substantially observed in most of all life forms. A molecular system to form the circadian rhythm in the body is referred to as the 'circadian clock.'

The circadian rhythm is closely associated with the health of a living thing. Loss of the circadian rhythm occurring due to a malfunction of a normal circadian clock may cause a metabolic disease such as diabetes or hypertension and, occasionally, a serious disease such as cancer.

The smallest unit of configuring the human body is referred to as a 'cell.' The cell normally divides, grows and/or dies and is eliminated by internal control of the cell, thus balancing the number of cells. In case of damaging a cell due to any cause, the cell may be restored by some healing process and function again as a normal cell. On the other hand, the cell occasionally undergoes apoptosis if it could not be restored. However, when there is a variation in genes of cells owing to different reasons, some cells may be abnormally altered and show incomplete maturation and excess proliferation, and this may be defined by the term 'cancer.'

Further, cancer invades into surrounding tissues and organs and destroys the same, and is characterized by being transferred to other organs ('cancer metastasis'). Cancer may refer to cell proliferation which is out of control, and which destroys the structure and functions of normal cells and organs. Accordingly, it cannot be emphasized enough that diagnosis and treatment of cancers are very important.

Cancer treatment is generally classified into three kinds of treatment methods, that is, surgical treatment, anticancer chemotherapy, and radiation treatment. Further, local treatment, hormone therapy, photodynamic therapy, laser treatment, or the like have been also used. In recent years, even immunotherapy and gene therapy have been included. The surgical treatment may include, for example, radical surgery for attaining desired treatment effects, prophylactic surgery for obtaining protective effects, and palliative surgery for alleviating symptoms of the disease. Alternatively, the anticancer chemotherapy is a treatment method of using specific medicines to kill cancer cells, that is, anticancer drugs to cure the cancer, which is a systemic treatment method to be effective to cancer cells having spread through the whole body. Further, the radiation treatment is a treatment method of directly attacking a cancer mass in order to kill cancer cells.

With regard to the treatment of cancers, the anticancer chemotherapy is usually adopted as an optimal treatment method in clinical fields. The anticancer drugs may include, for example, cell-cycle-specific drugs acting on cells only at a specific period of time in a cell cycle (ex., acting on M or S phase) and cell-cycle-nonspecific drugs acting on any cells under proliferation regardless of the cell cycle. In general, these anticancer drugs inhibit a synthetic process and mitotic division of DNA and RNA or, otherwise, produce harmful effects upon DNA molecules themselves, thus killing the cancer cells. However, although the anticancer chemotherapy attains effects of extending the lifetime of a cancer patient, this seriously affects some of normal cells having active cell division and proliferation, such as mucosa in the gastrointestinal track, hair, bone marrow, cells in a genital organ system, etc. as well as the cancer cells. In fact, after the anticancer chemotherapy is executed, the patient may suffer from anemia, reduction in numbers of white blood cells and/or blood platelets, cold sores in the mouth, and nausea, vomiting, diarrhea, or the like, and other serious side effects such as hair loss, reproductive dysfunction, etc. may also be caused.

In recent years, some scientists have proposed that the important factor affecting the survival of cancer patients is not the anticancer chemotherapy itself but a timing of applying the therapy to the patient, which would be a solution for considerably decreasing damage of DNA in normal cells. However, since a scientific background to support the above proposal is not sufficient, it is difficult to adopt this theoretical proposal in clinical fields.

Michele A. Gauger, Aziz Sancar. Cryptochrome, Circadian Cycle, Cell Cycle Checkpoints, and Cancer. Cancer Res 2005; 65:6828-34, have described that collapse of a circadian clock caused by DNA damage may influence a cell reaction and such influences may depend upon a mechanism of collapse of a bio-cycle.

SUMMARY

Accordingly, an aspect of the present invention is to provide a method for providing information that may be utilized to determine a time period when damaged DNA is rapidly restored, that is, a high restoration rate is detected, which includes providing information used for comparing restoration rates of damaged DNA.

In addition, another aspect of the present invention is to provide an apparatus capable of being utilized to determine a time period when a restoration rate is high, by providing information used for comparing restoration rates of damaged DNA.

Further, another aspect of the present invention is to provide an administration method of anticancer drugs.

Furthermore, another aspect of the present invention is to provide an anticancer supplement capable of considerably reducing side effects occurring due to administration of the anticancer drug.

The above aspect of the present invention will be achieved by the following characteristics:

(1) An administration method of an anticancer drug, including: administering cryptochrome or a cryptochrome inducing material to a patient suffering from a cancer ('cancer patient') to promote activation of Ataxia telangiectasia and Rad3 related ('ATR'); and administering an anticancer drug to the cancer patient having accelerated ATR activity.

(2) The method according to above (1), wherein cryptochrome is crypochrome 1 (Cry1).

(3) The method according to above (1), wherein the cryptochrome inducing material is at least one selected from a group consisting of N-[3-(9H-carbazol-9-yl)-2-hydroxypropyl]-N-(2-furanylmethyl)-methanesulfonamide, and N-[3-(9H-carbazol-9-yl)-2-hydroxypropyl]-N-(2-iodophenyl)-methanesulfonamide.

(4) The method according to above (1), further administering Timeless (Tim) while administering cryptochrome or the cryptochrome inducing material.

(5) An administration method of an anticancer drug, including: acquiring information about an expression level of cryptochrome from a sample taken from a cancer patient; and administering an anticancer drug to the cancer patient in a time period within a 24 hour cycle of cryptochrome obtained from the sample, wherein the expression level of cryptochrome is higher than the average expression level thereof.

(6) The method according to above (5), wherein the anticancer drug is administered in such a manner that the anticancer drug reaches a liver in a time period within the 24 hour cycle of cryptochrome, wherein the expression level of cryptochrome is increased to the highest amount.

(7) The method according to above (5), wherein cisplatin is administered by intraperitoneal injection (i.p. injection) 2 hours before the time period within the 24 hour cycle of cryptochrome, wherein the expression level of cryptochrome is increased to the highest amount.

(8) The method according to above (5), wherein cryptochrome is cryptochrome 1 (Cry1).

(9) The method according to above (5), wherein the information about an expression level of cryptochrome is acquired after forskolin treatment of the sample and synchronization of a bio-cycle of cells contained in the sample.

(10) The method according to above (5), further including acquiring information about a time period when activation of Ataxia telangiectasia and Rad3 related ('ATR') is accelerated, on the basis of the information about an expression level of cryptochrome.

(11) The method according to above (10), wherein the information about ATR activation is acquired by identifying the activity of at least one protein selected from phosphorylated-checkpoint kinase 1 (p-Chk1) and phosphorylated-protein 53 (p-p53).

(12) The method according to above (10), wherein the information about ATR activation is acquired by identifying the activity of phosphorylated-minichromosome maintenance protein 2 (p-MCM2).

(13) An anticancer supplement, including cryptochrome or a cryptochrome inducing material, in order to promote activation of Ataxia telangiectasia and Rad3 related ('ATR'), and thus inhibit side effects of an anticancer drug, when dosing with the above supplement.

(14) The anticancer supplement according to above (13), wherein cryptochrome is cryptochrome 1.

(15) The anticancer supplement according to above (13), wherein the cryptochrome inducing material is at least one selected from a group consisting of: N-[3-(9H-carbazol-9-yl)-2-hydroxypropyl]-N-(2-furanylmethyl)-methanesulfonamide, and N-[3-(9H-carbazol-9-yl)-2-hydroxypropyl]-N-(2-iodophenyl)-methanesulfonamide

(16) The anticancer supplement according to above (13), further including Timeless (Tim).

According to the present invention, information about a time period when Ataxia telangiectasia and Rad3 related ('ATR') activation is accelerated, on the basis of alternative information about an expression level of cryptochrome may be acquired, therefore, it can be determined that a restoration rate of damaged DNA is high at a time period when the expression level of cryptochrome is high. Accordingly, a time period when a restoration rate of DNA damaged by different causes is high, can be determined. Further, it is possible to estimate a time period when side effects occurring due to using an anticancer drug are minimized, and then, utilize the estimated result in determining the timing of administration of an anticancer drug.

Alternatively, the anticancer supplement according to the present invention contains cryptochrome or a cryptochrome inducing material to activate restoration of damaged DNA, thereby reducing side effects occurring due to administering the anticancer drug.

BRIEF DESCRIPTION OF THE DRAWINGS

The above and other aspects, features and other advantages of the present invention will be more clearly understood from the following detailed description taken in conjunction with the accompanying drawings, in which:

FIG. 6 is a block-diagram illustrating the technical configuration of an apparatus for provision of information to determine an administration timing of an anticancer drug according to one embodiment of the present invention.

DETAILED DESCRIPTION

Figure 1A:
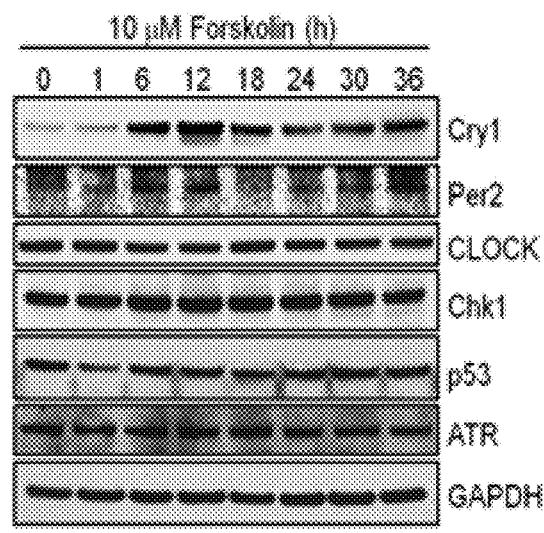
FIG. 1A illustrates expression levels of Cry1, Per2, CLOCK, Chk1, p53, ATR and GAPDH, respectively, in NIH3T3 cells which have bio-cycles synchronized by forskolin treatment.

The present invention discloses a method for providing information used for comparing restoration rates of damaged DNA, wherein information about a time period when Ataxia telangiectasia and Rad3 related ('ATR') activation is accelerated, on the basis of alternative information about an expression level of cryptochrome may be acquired, therefore, it can be determined that a restoration rate of damaged DNA is high at a time period when the expression level of cryptochrome is high. Accordingly, a time period when a restoration rate of DNA damaged by different causes is high, can be determined. Further, it is possible to estimate a time period when side effects occurring due to using an anticancer drug are minimized, and then, utilize the estimated result in determining the timing of administration of an anticancer drug.

Hereinafter, the present invention will be described in detail with reference to the accompanying drawings.

<Method for Providing Information used for Comparing Restoration Rates of Damaged DNA>

The present invention provides a method for providing information used for comparing restoration rates of damaged DNA, which includes; acquiring information about a time period when activation of Ataxia telangiectasia and Rad3 related ('ATR') is accelerated, on the basis of alternative information about an expression level of cryptochrome.

The information about the expression levels of cryptochrome may be acquired from any one selected from a group consisting of whole blood, serum, plasma, saliva, sputum, cerebrospinal fluid, red blood cells (erythrocyte), white blood cells (leukocyte), urine, feces, bronchial washing fluid, tear, nipple aspirate, lymph, micro-needle aspirate, any other body fluids, tissue samples, and cell extracts thereof, however, not be particularly limited thereto.

A mechanism for restoration of DNA damage mostly involves Ataxia telangiectasia and Rad3 related (hereinafter, referred to as 'ATR'), and ATR is a phosphorylation enzyme to recognize replication stress including DNA damage caused by UV radiation during a DNA damage checkpoint reaction and to phosphorylate damage restoring proteins.

The present inventors have found that the activity of ATR is substantially accompanied with information about an expression level of cryptochrome.

More particularly, the activity of ATR complies with the information about an expression level of cryptochrome 1. In particular, the activity of ATR is increased in a time period when the expression level of cryptochrome 1 is high, whereas the ATR activity is decreased in a time period when the expression level of cryptochrome 1 is low.

In other words, it can be determined that a time period when the expression level of cryptochrome 1 is high may be a time period when activation of ATR ('ATR activation') is accelerated. Further, as described above, ATR takes part in the mechanism for restoration of DNA damage. Therefore, it can be determined that the damaged DNA is rapidly restored (that is, a restoration rate of damaged DNA is high) if ATR activation is accelerated. Accordingly, it may be possible to provide information indicating that a sample with a high expression level of cryptochrome may exhibit a higher restoration rate of damaged DNA, as compared to another sample with a relatively lower expression level of the same.

The information about an expression level of cryptochrome may be acquired from a sample taken every hour or from another sample cultured under an environment where a 24 hour bio-cycle of cells contained in the sample can be present.

The cells contained in the sample are not particularly limited but may include, for example; epithelial cells, fibroblasts, endothelial progenitor cells, endothelial cells, proangiogenic marrow cells, dendritic cells, or the like.

Obtaining the information from the sample cultured under an environment where a 24 hour bio-cycle of the cells contained in the sample may include, for example, provision of the information from a sample that contains cells having a bio-cycle synchronized by forskolin treatment.

The synchronization of the bio-cycle stated in the present disclosure means formation of a standard 24 hour cycle in order to present the same 24 hour bio-cycle as in the body.

Information about ATR activation may be acquired by identifying the activity of an ATR activating marker. For instance, identifying at least one protein among phosphorylated-checkpoint kinase 1 (p-Chk1) and phosphorylated-protein 53 (p-p53) may obtain the information as described above. Alternatively, the information may be acquired by identifying the activity of phosphorylated-minichromosome maintenance protein 2 (p-MCM2).

Aspects to be employed in the method for providing information used for comparing of restoration rates of damaged DNA may include mammals, for example, a human being, as well as non-human primate; livestock such as dog, cat, sheep, cow, goat, pig, horse, etc.; experimental animals such as mouse, rat, rabbit, guinea pig, etc.; and the like.

As described above, the present invention may acquire information about a time period when ATR activation is accelerated, on the basis of alternative information about an expression level of cryptochrome, therefore, provide information indicating that a sample with a high expression level of cryptochrome may exhibit a higher restoration rate of damaged DNA, as compared to another sample with a relatively lower expression level of cryptochrome.

In addition, using the method for providing information used for comparing restoration rates of damaged DNA according to the present invention, a time period when damaged DNA is rapidly restored may be identified and thus utilized to determine a time period when a high restoration rate of DNA damaged by a variety of causes is exhibited.

For instance, DNA in a normal cell is sometimes damaged due to side effects of an anticancer drug. If the present invention is employed, a time period when damaged DNA due to side effects of the anticancer drug is rapidly restored, may be identified. That is, it is possible to acknowledge a time period when side effects caused by administration of an anticancer drug are considerably less and, as a result, an optimum timing of administration of the anticancer drug can be determined.

More particularly, since ATR activation is accelerated in a time period wherein an expression level of cryptochrome 1 is high, it can be determined that such a time period as described above (wherein an expression level of cryptochrome 1 is high) is an appropriate timing of administration of an anticancer drug. Preferably, it is determined that administering an anticancer drug as early as a period of time from the time period wherein an expression level of cryptochrome 1 is high until the administered anticancer drug reaches the liver, may be an optimum timing of administration of the anticancer drug.

Metabolism of the anticancer drug is usually executed in the liver and a certain time is required until the anticancer drug reaches the liver. Accordingly, in a case where the anticancer drug is administered earlier as described above, the anticancer drug may reach the liver in a time period wherein an expression level of cryptochrome 1 is high, thereby minimizing side effects of the anticancer drug. For instance, in case of cisplatin as an anticancer drug widely used in the related art, it takes about 2 hours until this drug reaches the liver by intraperitoneal injection (that is, i.p. injection). Therefore, if cisplatin is administered 2 hours before the time period wherein an expression level of cryptochrome 1 is increased to the highest amount, side effects of the anticancer drug can be minimized.

<Apparatus for Provision of Information for Comparing Restoration Rates of Damaged DNA>

In addition, the present invention provides an apparatus for provision of information used for comparing restoration rates of damaged DNA. Hereinafter, one embodiment of the apparatus for provision of information used for comparing restoration rates of damaged DNA will be described in more detail.

An apparatus for provision of information 100 which is used for determining an optimum timing of administration of an anticancer drug, according to the present invention, includes a receiving unit 110, an information acquiring unit 120 and an output unit 130.

The receiving unit 110 receives a sample from which information about an expression level of cryptochrome is acquired.

Such a sample as described above may include, for example, whole blood, serum, plasma, saliva, sputum, cerebrospinal fluid, erythrocytes, leukocytes, urine, feces, bronchial washing fluid, tear, nipple aspirate, lymph, microneedle aspirate, any other body fluids, tissue samples, and cell extracts thereof, however, not be particularly limited thereto.

The information acquiring unit 120 obtains the information about an expression level of cryptochrome from the sample received in the receiving unit 110, and then, acquire alternative information about a time period when ATR activation is accelerated.

Acquiring the information about an expression level of cryptochrome in the information acquiring unit 120, and the information about a time period when ATR activation is accelerated, may be achieved by the same process as the method for providing information used for comparing restoration rates of damaged DNA, which has been already described above.

The output unit 130 outputs information about the time period when ATR activation is accelerated, obtained from the information acquiring unit 120.

As described above, the apparatus for provision of information used for comparing restoration rates of damaged DNA according to the present invention may obtain information about a time period when ATR activation is accelerated, on the basis of information about an expression level of cryptochrome, and therefore, provide information identifying that a sample with a high expression level of cryptochrome, as compared to another sample with a relatively lower expression level of the same.

In addition, the apparatus for provision of information used for comparing restoration rates of damaged DNA may be used to identify a time period at which a high restoration rate of damaged DNA is exhibited, and therefore, can be utilized to determine when DNA damaged by a variety of causes is rapidly restored.

For instance, DNA in a normal cell is sometimes damaged due to side effects of an anticancer drug. If the present invention is employed, a time period when damaged DNA due to side effects of the anticancer drug is rapidly restored, may be identified. That is, it is possible to acknowledge a time period when side effects caused by administration of an anticancer drug are considerably less and, as a result, an optimum timing of administration of the anticancer drug can be determined.

More particularly, since ATR activation is accelerated in a time period wherein an expression level of cryptochrome 1 is high, it can be determined that such a time period as described above (wherein an expression level of cryptochrome 1 is high) is an appropriate timing of administration of an anticancer drug. Preferably, it is determined that administering an anticancer drug as early as a period of time from the time period wherein an expression level of cryptochrome 1 is high until the administered anticancer drug reaches the liver, may be an optimum timing of administration of the anticancer drug.

Metabolism of the anticancer drug is usually executed in the liver and a certain time is required until the anticancer drug reaches the liver. Accordingly, in case where the anticancer drug is administered earlier as described above, the anticancer drug may reach the liver in a time period wherein an expression level of cryptochrome 1 is high, thereby minimizing side effects of the anticancer drug. For instance, in case of cisplatin as an anticancer drug widely used in the related art, it takes about 2 hours until this drug reaches the liver at i.p. administration. Therefore, if cisplatin is administered 2 hours before the time period wherein an expression level of cryptochrome 1 is increased to the highest amount, side effects of the anticancer drug can be minimized.

<Administration Method of Anticancer Drug>

Further, the present invention provides a method of administrating an anticancer drug.

The method of administering an anticancer drug according to one embodiment of the present invention may include: administering cryptochrome or a cryptochrome inducing material to a cancer patient to promote activation of Ataxia telangiectasia and Rad3 related ('ATR'); and administering an anticancer drug to the cancer patient under a status of promoting the activity of ATR.

Hereinafter, a method for administration of an anticancer drug according to one embodiment of the present invention will be described in more detail.

At first, cryptochrome or a cryptochrome inducing material is administered to a cancer patient to promote ATR activation.

As described above, since ATR activation is increased in a time period wherein cryptochrome is highly expressed and damage restoration is rapidly achieved, a mechanism for restoration of DNA damage may be activated by administering cryptochrome or any cryptochrome inducing material to a cancer patient.

More particularly, cryptochrome may be cryptochrome 1.

Also, the cryptochrome inducing material is not particularly limited so far as it can promote expression of cryptochrome and may include, for example, N-[3-(9H-carbazol-9-yl)-2-hydroxypropyl]-N-(2-furanylmethyl)-methanesulfonamide, N-[3-(9H-carbazol-9-yl)-2-hydroxypropyl]-N-(2-iodophenyl)-methanesulfonamide, or the like, which may be used alone or in combination with two or more thereof.

If it is necessary, Timeless (Tim) may be further administered when administering cryptochrome or a cryptochrome inducing material.

The above description is based on such findings of the present inventors that cryptochrome 1 interacts with Tim to promote the activity of ATR. More particularly, Tim is administered together with cryptochrome 1, the activity of ATR may be further accelerated owing to interaction between both of these compounds, thereby further activating a mechanism for restoration of DNA damage.

Thereafter, an anticancer drug is administered to the cancer patient having accelerated ATR activity.

When the anticancer drug is administered to the cancer patient having accelerated ATR activity, a DNA damage checkpoint reaction is actively executed by ATR activation even though DNA of a normal cell is damaged by administration of the anticancer drug, thereby minimizing side effects of the anticancer drug.

The method for administration of an anticancer drug according to one embodiment of the present invention includes: identifying information about an expression level of cryptochrome from a sample taken from a cancer patient to measure the same; and administering an anticancer drug to the cancer patient in a time period within a 24 hour cycle of cryptochrome obtained from the sample, wherein the expression level is higher than the average expression level thereof.

Hereinafter, a method for administration of an anticancer drug according to another embodiment of the present invention will be described in more detail.

At first, information about an expression level of cryptochrome is obtained from a sample taken from a cancer patient.

The information about an expression level of cryptochrome may be acquired from the sample taken per hour or from a sample cultured under an environment where a 24 hour bio-cycle of a cell contained in the sample can be present.

The cell contained in the sample is not particularly limited but may include, for example, epithelial cells, fibroblasts, endothelial progenitor cells, endothelial cells, pro-angiogenic marrow cells, dendritic cells, or the like.

Obtaining the information from the sample cultured under an environment where a 24 hour bio-cycle of the cells contained in the sample can be present may include, for example, provision of the information from a sample that contains cells having a bio-cycle synchronized by forskolin treatment.

The synchronization of the bio-cycle stated in the present disclosure means formation of a standard 24 hour cycle in order to present the same 24 hour bio-cycle as in the body.

As described above, an extent of ATR activation depends upon the information about an expression level of cryptochrome. Accordingly, the information about ATR activation may be acquired from the information about an expression level of cryptochrome, and this result may be attained by identifying the activity of an ATR activating marker. For instance, identifying the activity of at least one protein selected from phosphorylated-checkpoint kinase 1 (p-Chk1) and phosphorylated-protein 53 (p-p53) may acquire the above information. Alternatively, the above information may be acquired by identifying the activity of phosphorylated-minichromosome maintenance protein 2 (p-MCM2).

Following this, an anticancer drug may be administered to the cancer patient in a time period within a 24 hour bio-cycle of cryptochrome obtained from the above sample, wherein an expression level of cryptochrome is higher than the average expression level thereof.

As described above, the activity of ATR taking part in the mechanism for restoration of DNA damage is accompanied with the information about an expression level of cryptochrome. More particularly, it depends upon an expression cycle of cryptochrome 1 such that the activity of ATR is increased in a time period wherein an expression level of cryptochrome 1 is high, whereas the activity of ATR is decreased in another time period wherein the expression level of cryptochrome 1 is low.

In other words, since a time period when the expression level of cryptochrome 1 is high may be a time during which ATR activation is accelerated, a mechanism for restoration of DNA damage is actively performed if the anticancer drug is administered in a time period within the 24 hour bio-cycle of cryptochrome 1, wherein the expression level of cryptochrome is high, thereby considerably reducing side effects occurring due to administration of an anticancer drug.

The method for administration of an anticancer drug according to present invention may enable administration of an anticancer drug in such a manner that the anticancer drug reaches the liver in a time period within the 24 hour cycle of cryptochrome, wherein the expression level of cryptochrome is high, more particularly, in a time period of the day wherein the expression level of cryptochrome is increased to the highest amount.

Metabolism of the anticancer drug is usually executed in the liver and a certain time is required until the anticancer drug reaches the liver. Accordingly, if the anticancer drug is administered earlier such that the anticancer drug reaches the liver in a time period wherein an expression level of cryptochrome is high, side effects of the anticancer drug may be minimized.

Preferably, the anticancer drug is administered in such a manner that the anticancer drug reaches the liver in a time period within the 24 hour cycle of cryptochrome, wherein the expression level of cryptochrome is increased to the highest amount. A time required until the anticancer drug reaches the liver may depend upon types of anticancer drugs, administering methods, or the like, therefore, it is appropriately selected or determined how early the anticancer drug should be administered. For instance, in case of administering cisplatin by i.p. injection, this drug can be administered 2 hours before the time when the expression level of cryptochrome is increased to the highest amount.

<Anticancer Supplement>

Further, the present invention provides an anticancer supplement, which includes: cryptochrome or any cryptochrome inducing material to promote activation of Ataxia telangiectasia and Rad3 related ('ATR'), and thus inhibit side effects of an anticancer drug when dosing with the above supplement.

As described above, since ATR activity is increased in a time period wherein an expression level of cryptochrome is high to thus rapidly restore DNA damage, the anticancer supplement containing cryptochrome or any cryptochrome inducing material may activate a mechanism for restoration of DNA damage, thereby inhibiting side effects occurring due to administration of the anticancer drug.

In particular, Cryptochrome may be cryptochrome 1.

The cryptochrome inducing material is not particularly limited so far as it can promote expression of cryptochrome, and may include, for example, N-[3-(9H-carbazol-9-yl)-2-hydroxypropyl]-N-(2-furanylmethyl)-methanesulfonamide, N-[3-(9H-carbazol-9-yl)-2-hydroxypropyl]-N-(2-iodophenyl)-methanesulfonamide, or the like, which may be used alone or in combination with two or more thereof.

If it is necessary, the anticancer supplement of the present invention may further include Timeless ('Tim').

The above description is based on such findings of the present inventors that cryptochrome 1 interacts with Tim to promote the activity of ATR. More particularly, Tim is further included, the activity of ATR may be further accelerated owing to interaction between both of these compounds, thereby more activating a mechanism for restoration of DNA damage.

The anticancer supplement used herein may be formulated into a variety of forms including, for example: oral formulations such as powder, granules, tablets, capsules, suspension, emulsion, syrup, aerosol, etc.; topical preparations; suppositories; or sterile injectable solution, or the like, according to any conventional method.

Carriers, excipients and diluents possibly included in the above anticancer supplement of the present invention may include, for example, lactose, dextrose, sucrose, sorbitol, mannitol, xylitol, erythritol, maltitol, starch, acacia rubber, alginate, gelatin, calcium phosphate, calcium silicate, cellulose, methyl cellulose, amorphous cellulose, polyvinyl pyrrolidone, water, methyl hydroxybenzoate, propyl hydroxybenzoate, talc, magnesium stearate and mineral oil.

The formulation may be prepared using any of fillers, bulk additives, binders, humectants, disintegrants, diluents such as surfactants, or excipients generally used in the related art.

In case of a solid formulation used for oral administration, tablets, pills, powder, granules, capsules, etc. may be included, and the solid formulation may be prepared by adding at least one excipient, for example, starch, calcium carbonate, sucrose, lactose, gelatin, etc. to the obtained extract. In addition to a simple excipient, a lubricant such as magnesium stearate, talc, etc. may also be used. Alternatively, a liquid formulation used for oral administration may include, for example, suspension, internal solution, emulsion, syrup, etc., and simple diluents commonly used in the related art such as water, liquid paraffin, or other different excipients, for example, a wetting agent, a sweetening agent, aromatics, preservatives, or the like, may also be included.

Formulations for parental administration may include, for example, sterile water solution, non-aqueous solvent, suspension, emulsion, lyophilized formulations and suppositories.

The non-aqueous solvent or suspension used herein may include, for example, propylene glycol, polyethylene glycol, vegetable oil such as olive oil, injectable ester such as ethyloleate, or the like.

Basic materials for suppositories may include, for example, witepsol, macrogol, tween 61, cacao butter, laurinum, glycerogelatin, or the like.

Furthermore, among other suitable methods used in the related art, the method disclosed in Remington's Pharmaceutical Science, Mack Publishing Company, Easton Pa., may be used to produce appropriate formulations.

Hereinafter, preferred embodiments will be described to more concretely understand the present invention. However, it will be apparent to those skilled in the related art that such embodiments are provided for illustrative purposes without particular limitation to the appended claims, various modifications and alterations may be possible without departing from the scope and spirit of the present invention, and such modifications and alterations are duly included in the present invention as defined by the appended claims.

Hereinafter, the present invention will be more concretely understood according to the following examples.

Example

1. Preparation of Material and Experiments (1) Cell Culture, Bio-cycle Synchronization, UV Radiation and Transduction For cell culture, 1 ml of 10% (vol/vol) fetal bovine serum (FBS, Hyclone Co.) was added to 10 ml of Dulbecco's modified Eagle's medium (DMEM), followed by adding 100 µl of 1% (vol/vol) penicillin-streptomycin thereto. Then, NIH3T3 cells, wild-type mouse embryo fibroblasts (WT MEFs), and mouse embryo fibroblasts free from cryptochrome 1 (Cry1) and cryptochrome 2(Cry2) (Cry$^{DKO}$ MEFs), respectively, were cultured in the above prepared culture medium.

For bio-cycle synchronization, fused cells were further cultured for additional three (3) days after adding 10 mM forskolin to the above medium.

For UV radiation, using a germicidal lamp (GE) mainly emitting UV-C beam, UV light was emitted to the fused cells by 5 J/m$^2$. Then, a fluorescence rate of the incident beam was measured using a UV-C sensor.

For transduction of DNA constructs and ON-TARGET plus SMART pool small interfering RNA duplexes, lipofectamine 2000 (Invitrogen) was used.

(2) Treatment of Mouse and Preparation of Liver Tissue of Mouse

Before sacrificing C57BL/6J male mouse, the animal was placed under an environment where the daytime and nighttime were maintained for 12 hours each night were maintained for 12 hours, respectively, during 2 weeks.

After exposing the mouse to $CO_2$ and putting the animal to death, the liver of the mouse was cut into pieces having a size of less than 2 mm and washed with phosphate buffer saline (PBS), followed by freezing the same in liquid nitrogen. The frozen liver piece was pulverized using a ceramic mortar and pestle under liquid nitrogen to prepare a whole cell fusion.

(3) Immunoblotting and Immunoprecipitation

An extract of cytoplasm and nucleus protoplasm as well as the whole cell fusion were prepared. A chromatin-rich part could be obtained by treating 10-U DNase I (Promega) and 100-U micrococcal nuclease at 30° C. for 30 minutes and from the nucleus protoplasm through extraction using fillets. Each part was analyzed by SDS-PAGE and both of Ponceau S staining and immunoblotting. According to typical immunoblotting orders, amounts of proteins were determined using the above parts. For quantification of the immunoblotting, ImageQuant 5.2 software (Molecular Dynamics) was used.

Antibodies used in the experiments were as follows: GAPDH, p-Chk1 5345, p53, p-p53 S15 (Cell Signaling Technology), ATR, RPA70 (Replication Protein A), Chk1, Actin (Santa Cruz Biotechnology), Clock, Cry1, Cry2, p-MCM2 5108, Tim (Timeless), Tipin (Bethyl Laboratory), histone H3 (Millipore), Per2 (BD Biosciences) and platinum GpG (Oncolyze). Tim and Cry1, Tim protein complexes were precipitated using protein A/G-coupled sepharose (Sigma) collected beforehand as well as an anti-Tim antibody. In order to detect Cry1 precipitated together with Tim, immunoblotting was implemented.

(4) Immunocytochemistry

For immunofluorescence staining, WT MEFs were cultured in a 15-mm glass chip coated with poly-D-lysine and laminin (BD Biosciences) using 50 to 60% confluency, while cells were treated with 10-mM forskolin for 54 hours.

(5) Immunoslot Blotting

After separating genomic DNA from MEFs cells using QIAamp DNA Mini kit (Qiagen), 1 mg of genomic DNA was moved to a nitrocellulose membrane by a BioDot SF Microfiltration apparatus (BioRad). The genomic DNA was heated at 80° C. for 2 hours under vacuum to be bound to the nitrocellulose membrane. Using a mono-antibody specifically recognizing Platinum-GpG adducts (Oncolyze), an amount of DNA damaged by cisplatin was relatively measured. Then, it may be identified whether DNA bound to the nitrocellulose membrane is quantified on Gel-doc after staining the DNA with Sybr-gold as a DNA staining reagent.

Figure 1B:
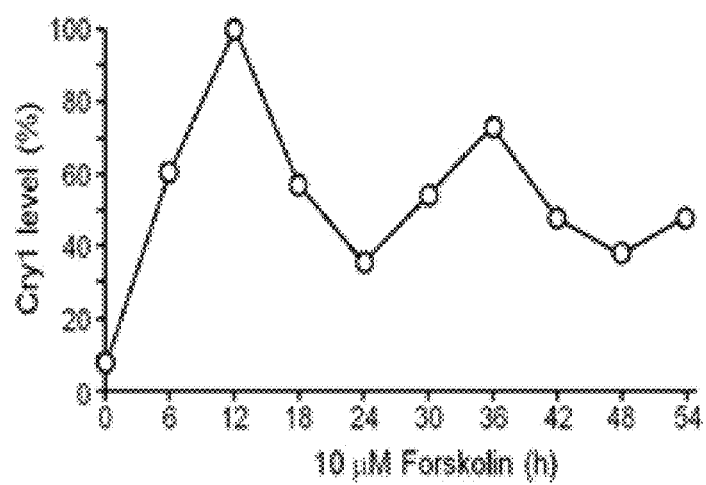
FIG. 1B illustrates analyzed results of Cry1 expression levels over time after the forskolin treatment as shown in FIG. 1A.
Figure 1C:
FIG. 1C illustrates expression levels of p-Chk1 and p-p53 in cells relative to UV exposure time, wherein the cells 12 hours and 24 hours after forskolin treatment, respectively.
Figure 1D:
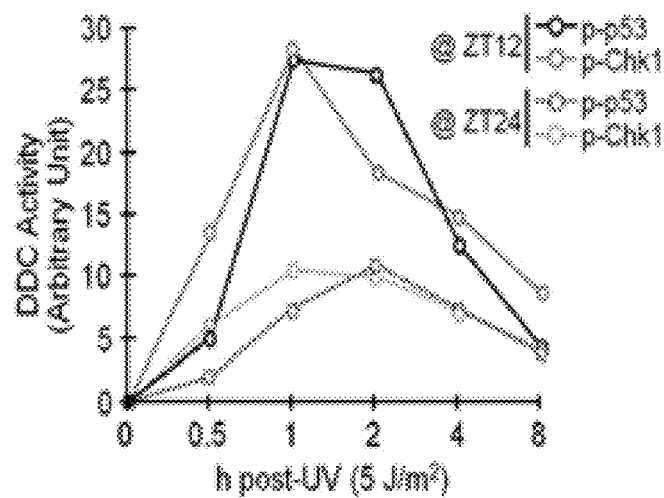
FIG. 1D illustrates activity for checking DNA damage shown in FIG. 1C.
Figure 1E:
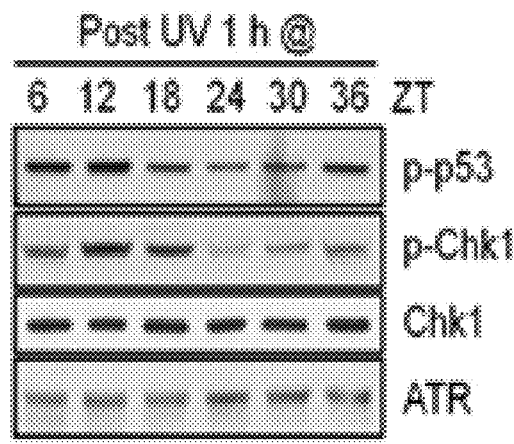
FIG. 1E illustrates expression levels of p-p53, p-chk1, chk1 and ATR, respectively, over time after forskolin treatment.
Figure 1F:
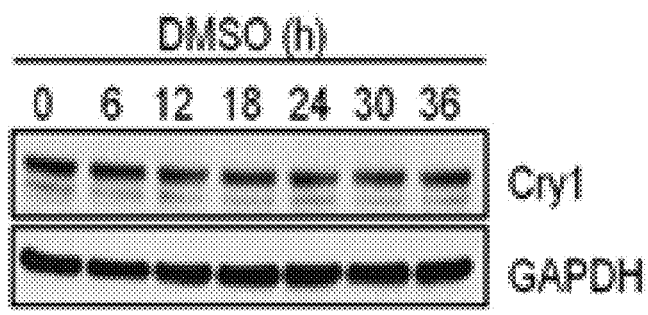
FIG. 1F illustrates expression levels of Cry1 and GAPDH, respectively, over time after dimethylsulfoxide treatment.
Figure 1G:
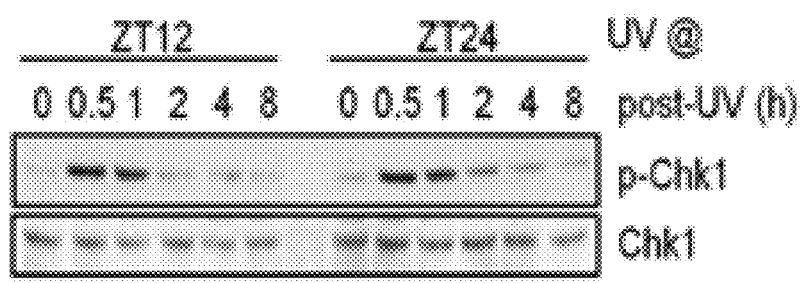
FIG. 1G illustrates expression levels of p-Chk1 and Chk1 in cells relative to UV exposure time, wherein the cells 12 hours and 24 hours after forskolin treatment, respectively.

2. Identification of Whether Bio-cycle Activity Controls ATR Signal Detonated by UV Radiation Damage As shown in FIG. 1A and FIG. 1B, forskolin treatment generates rhythmic Clock/Bmall activity in NIH3T3 cells, which in turn, induces an active bio-rhythm of cryptochrome 1 (Cry1) and Per2. Cryptochrome 1 (Cry1) exhibited a maximum activity and a minimum activity of 12 hours and 24 hours, respectively, after forskolin treatment. Other proteins did not show regular conditions.

In order to investigate whether the bio-cycle activity influences an ATR pathway, a cell 12 hours and another cell 24 hours after the forskolin treatment, respectively, were subjected to UV radiation in order to measure an extent of phosphorylation of p53 and Chk1 proteins as a proxy marker of ATR.

Depending upon an exposure time to UV light ('UV exposure time'), an extent of phosphorylation could be remarkably observed. More particularly, the cell 12 hours after the forskolin treatment exhibited a higher extent of phosphorylation by 2 to 3 times, as compared to the cell 24 hours after the forskolin treatment.

In order to identify whether such a reaction as described above is definitely controlled by the bio-cycle activity, intensities of phosphorylation extent over time after different forskolin treatments were measured. Since p-p53 and p-Chk1 showed the highest intensity of phosphorylation extent at 1 hour after exposure to UV radiation, cells were collected at 1 hour after exposure to UV radiation and subjected to assessment of phosphorylation extents.

In the experiment, oscillations of approximate bio-cycles of p-p53 and p-Chk1 were observed as a function to time. This result demonstrates that the bio-cycle activity is associated with formation of ATR signaling relative to stress of gene toxicity.

Expression levels of ATR, p53 and Chk1 were substantially not varied during synchronization of bio-cycles, therefore, it was presumed that variations in expression cycles of p-p53 and p-Chk1, respectively, do not occur by rhythmic expression of ATR, p53 and Chk1.

Further, as a result of analyzing ATR signaling of the cell treated with dimethylsulfoxide (DMSO), phosphorylation over UV exposure time was not clearly detected. The reason for this is considered to be due to the fact that DMSO inhibits forskolin effects to therefore prevent the bio-cyclic rhythm from being activated.

Accordingly, it is presumed that the bio-cycle activity may control ATR signaling derived from UV radiation-based damage.

3. Identification of Whether Cryptochrome 1 (Cry1) is a Control Factor of ATR Activity In order to identify whether ATR signaling is definitely influenced by the bio-cycle, extents of phosphorylation between WT MEFs and Cry$^{DKO}$ MEFs free from Cry1 and Cry2 were compared.

Figure 2A:
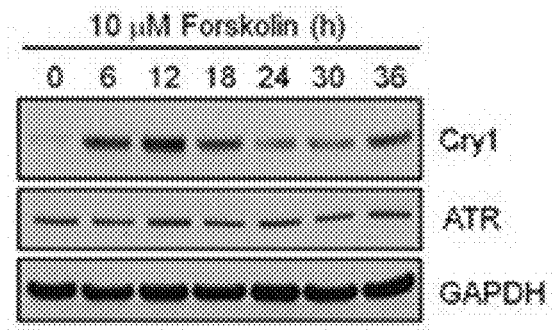
FIG. 2A illustrates expression levels of Cry1, ATR and GAPDH proteins, respectively, in MEFs cells which have bio-cycles synchronized by forskolin treatment.

Similar to NIH3T3 cells, as shown in FIG. 2A, it was found that cryptochrome 1 (Cry1) exhibited maximum and minimum expressions 12 hours and 24 hours after forskolin treatment, respectively. Further, as shown in FIG. 2B, it was found that ATR activity was remarkably increased relative to UV exposure time.

Figure 2B:
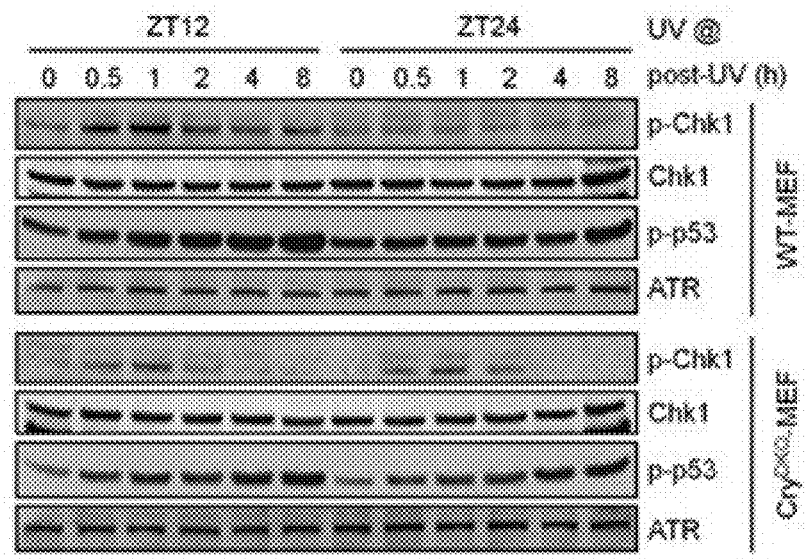
FIG. 2B illustrates expression levels of p-Chk1, Chk1, p-p53 and ATR, respectively, in WT MEFs and Cry$^{DKO}$ MEFs cells, relative to UV exposure time, wherein the cells 12 hours and 24 hours after forskolin treatment, respectively.

On the other hand, as shown in FIG. 2B, ATR activity of Cry$^{DKO}$ MEFs free from cryptochrome 1 (Cry1) and cryptochrome 1 (Cry2)) did not exhibit an activity cycle relative to UV exposure time.

Figure 2C:
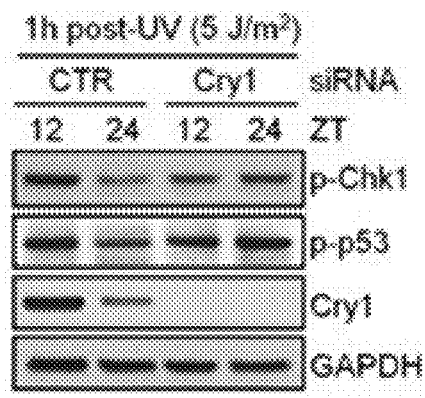
FIG. 2C illustrates expression levels of p-chk1, p-p53, cryptochrome 1 and GPDH in control (CTR) or cells free from Cry1, respectively, over time after forskolin treatment.

As can be seen in FIG. 2C, it was enough to eliminate ATR activity dependent upon a bio-cycle by removing cryptochrome 1 (Cry1) only from siRNA in WT MEFs. This demonstrates that cryptochrome 1 (Cry1) is a control factor of ATR activity regulated by the bio-cycle.

Figure 2D:
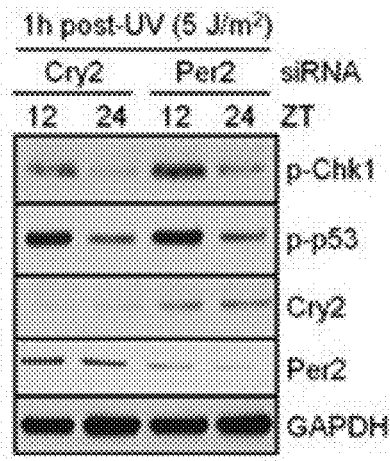
FIG. 2D illustrates expression levels of p-chk1, p-p53, cryptochrome, Per2 and GAPDH in cells free from Cry2 or Per2, respectively, over time after forskolin treatment.

As shown in FIG. 2D, since the ATR expression cycle is almost not influenced even if there is a lack of other major bio-cycle elements including Cry2 and Per2, it may be understood that cryptochrome 1 (Cry1) in cells responds to UV light-based damage and controls ATR activity.

Figure 2E:
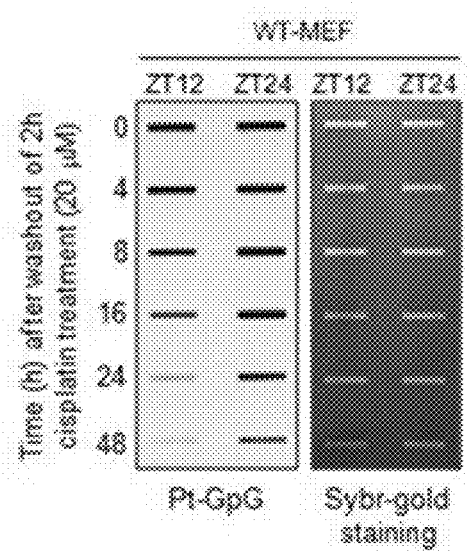
FIG. 2E illustrates expression levels of Platinum-GpG in WT MEFs cells, over time after administration of cisplatin, wherein the cells 12 hours and 24 hours after forskolin treatment, respectively.

As can be seen in FIG. 2E, it was found that a removal rate of Platinum-GpG is higher at 12 hours after forskolin treatment, as compared to that at 24 hours after the same. When cryptochrome 1 (Cry1) expression is the maximum, ATR activity also reaches a maximum level. Herein, a conclusion can be reached that DNA damaged by cisplatin is rapidly restored, as compared to the case of a minimum expression of cryptochrome 1 (Cry1).

4. Identification of Cryptochrome 1 (Cry1) Mechanism in Control of ATR Pathway In order to investigate interaction of Tim and cryptochrome (Cry1) relative to UV exposure time and DNA damage, immunoprecipitation analysis was executed.

Figure 3A:
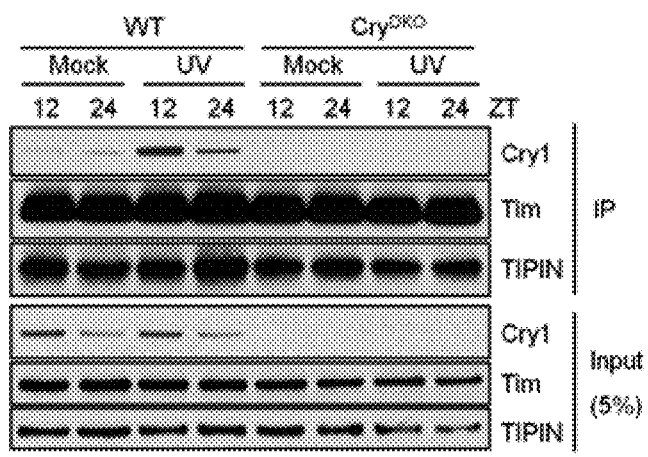
FIG. 3A illustrates analyzed results of expression levels of Cry1 and Tim in cells, relative to whether the cells were damaged by UV radiation or not, through immunoprecipitation, wherein the cells 12 hours and 24 hours after forskolin treatment, respectively.

As can be seen in FIG. 3A, if there is no DNA damage, an amount of cryptochrome 1 (Cry1) reacting with Tim was similar to that in WT MEFs regardless of bio-cycle. However, when gene toxicity damage occurred, an amount of cryptochrome 1 (Cry1) reacting with Tim was increased, as compared to in a case of no occurrence of DNA damage. Further, when DNA was damaged, the amount of cryptochrome 1 (Cry1) was varied over time.

The expression level of cryptochrome 1 (Cry1) at 12 hours after forskolin treatment was higher and an amount of cryptochrome 1 (Cry1) reacting with Tim was further increased, as compared to that at 24 hours after forskolin treatment when the amount of cryptochrome 1 (Cry1) is relatively decreased. A hypothesis that cryptochrome 1 (Cry1) may function as a time gated linker in the interaction between Tim and ATR since Tim is required for appropriate ATC activity, has been developed.

Figure 3B:
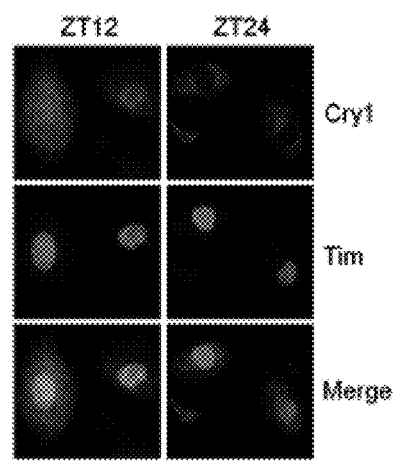
FIG. 3B illustrates locations of Cry1 and Tim in cells over time through immuno-fluorescence, wherein the cells 12 hours and 24 hours after forskolin treatment, respectively.

As can be seen in FIG. 3B, locations of cryptochrome 1 (Cry1) and Tim in the cell were analyzed and it was found that cryptochrome 1 (Cry1) is located in a cell nucleus at 12 hours or later after forskolin treatment and in the cytoplasm at 24 hours or later after forskolin treatment, respectively, as compared to the fact that Tim expression is mostly exhibited in the cell nucleus independently of a bio-cycle time. Therefore, it can be understood that the interaction between cryptochrome 1 (Cry1) and Tim in the nucleus is associated with ATR activity.

In order to investigate such possibilities as described above, $Cry^{DKO}$ was subjected to isoform expression of Cry1, and ATR activity relative to location of cryptochrome 1 (Cry1) and UV light-based damage was analyzed.

Figure 3C:
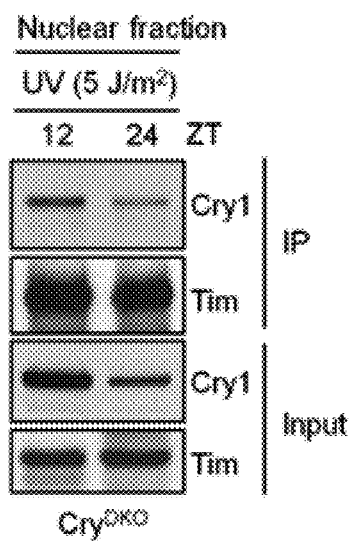
FIG. 3C illustrates analyzed results of expression levels of cryptochrome 1 (Cry1) and Tim in $Cry^{DKO}$ cells, wherein the cells have undergone isoform expression of Cry1, and 12 hours and 24 hours after forskolin treatment, respectively.
Figure 3D:
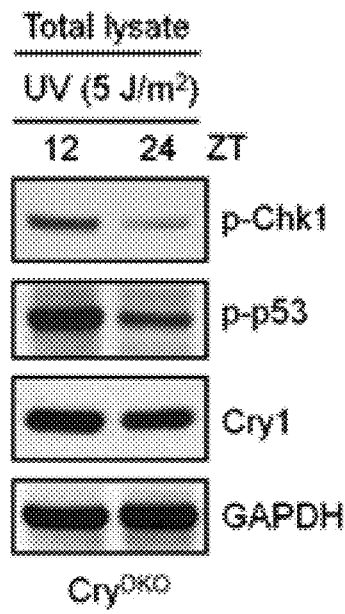
FIG. 3D illustrates expression levels of p-Chk1, p-p53, cryptochrome 1 and GAPDH in $Cry^{DKO}$ cells, wherein the cells 12 hours and 24 hours after forskolin treatment, respectively.

As can be seen in FIG. 3C, an amount of cryptochrome 1 (Cry1) in the nucleus was more increased and an amount of cryptochrome 1 (Cry1) precipitated together with Tim was also more increased at 12 hours after forskolin treatment, as compared to that at 24 hours after forskolin treatment. Further, as can be seen in FIG. 3D, ATR activity defined by amounts of p-Chk1 and p-p53 was controlled to a higher level at 12 hours after forskolin treatment, as compared to that at 24 hours after forskolin treatment. Consequently, a conclusion can be reached that cryptochrome 1 (Cry1) present in a nucleus may influence ATR activity controlled by a bio-cycle through a temporary interaction between cryptochrome 1 (Cry1) and Tim.

5. Expression of Cryptochrome 1 (Cry1) Relative to CT

Cisplatin, an anticancer drug to activate ATR pathway, undergoes metabolism in the liver. When a mouse was bred in an environment where the daytime and nighttime were maintained for 12 hours each in order to induce a certain bio-cyclic rhythm, the bio-cyclic rhythm showed active expression of Cryptochrome 1 (Cry1).

In the present disclosure, CT refers to a time having passed from a time period when the bio-cyclic rhythm was induced. For instance, CT08 means 8 hours after the induction of the bio-cyclic rhythm, and CT20 means 20 hours after the induction of the bio-cyclic rhythm. Since the bio-cycle is of 24 hours, CT24 may substantially exhibit the same bio-cyclic rhythm as at CT0.

Figure 4A:
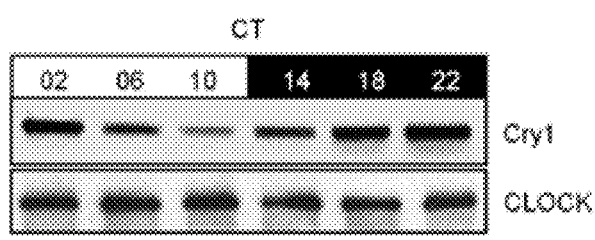
FIG. 4A illustrates expression levels of cryptochrome 1 and CLOCK relative to CT, respectively.
Figure 4B:
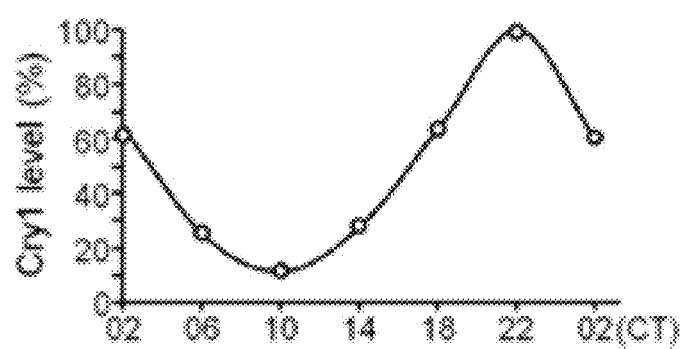
FIG. 4B illustrates analyzed results of the expression level of cryptochrome 1 shown in FIG. 4A.

It was found that the expression of Cry1 was the lowest at CT10 while being the highest at CT22. According to pharmacokinetic data, it takes about 2 hours until cisplatin reaches the liver by i.p. injection, therefore, CT08 and CT20 were selected. Accordingly, as can be seen in FIG. 4B, it may be presumed that cisplatin can influence the liver at CT10 and TT22 at which the expression of cryptochrome 1 (Cry1) was the lowest and highest, respectively.

Figure 4C:
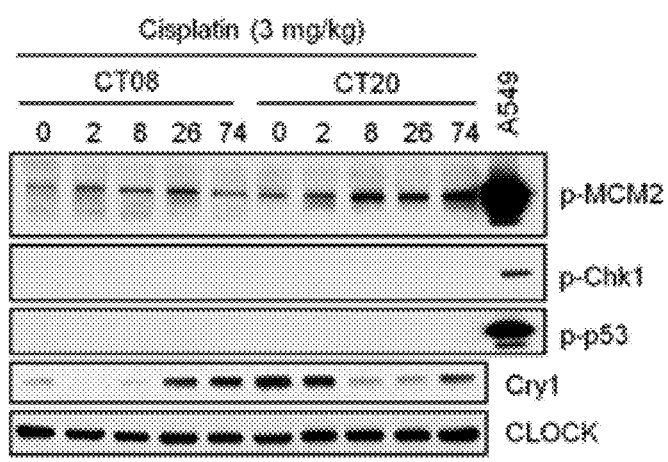
FIG. 4C illustrates expression levels of p-MCM2, p-chk1, p-p53, cryptochrome 1 and CLOCK relative to CT, respectively, if cisplatin was injected.
Figure 4D:
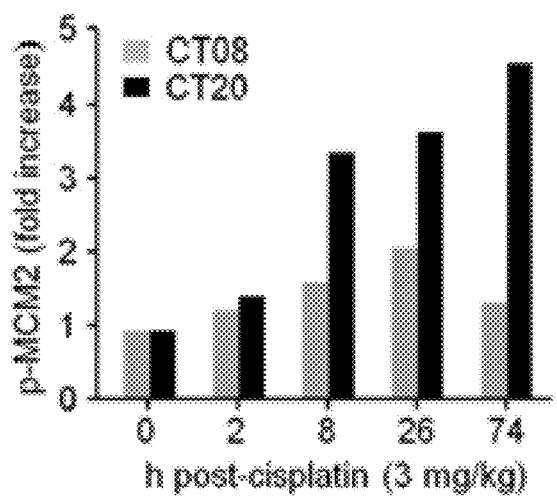
FIG. 4D illustrates expression levels of p-MCM2 over time after cisplatin was administered at CT08 and CT20, respectively.

However, as can be seen in FIG. 4C, extents of expression of p-Chk1 and p-p53 were insignificant. The reason of this fact is considered because the extents of expression of the above proteins in the liver of a mouse are relatively low. Instead, it was found that another ATR substrate, i.e., p-MCM2 S108 exhibited a clearly different expression aspect over time after cisplatin injection. From quantification investigation, the mouse at CT20 showed a stronger p-MCM2 signal by 2 times or more at 8 hours or later after the cisplatin injection, as compared to the mouse at CT08. Accordingly, the liver cell more closely responds to the stress of gene toxicity through the ATR pathway along with the level of cryptochrome 1 (Cry1).

Figure 5:
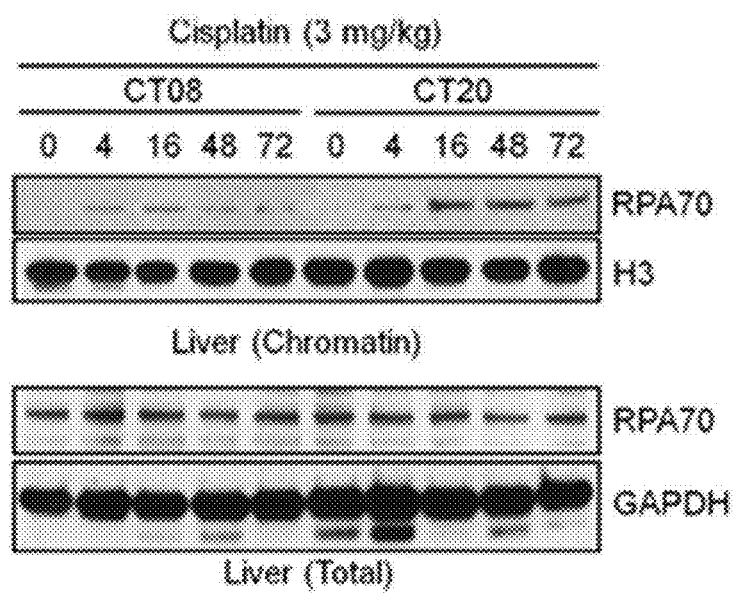
FIG. 5 illustrates expression levels of RPA70 in liver chromatin and the whole liver over time after cisplatin was administered at CT08 and CT20, respectively.

The ATR pathway takes part in, specifically, DNA repair as a nucleotide excision repair (NER) process. As can be seen in FIG. 5, accumulation of replicated protein A was identified in chromatin after cisplatin injection at CT20. This result suggests that ATR activity continuing at CT20 may have originated from a long term exposure of a specific substrate of ATR, that is, RPA-coated single strand gap having undergone NER.

What is claimed is:

1. An administration method of an anticancer drug with a use of an apparatus comprising a receiving unit, an information acquiring unit and an output unit, the method comprising:
   receiving a sample taken from a cancer patient in the receiving unit;
   measuring an expression level of cryptochrome 1 from the sample, and determining a time period within a 24 hour cycle of cryptochrome 1 when Ataxia telangiectasia and Rad3 related ('ATR') activation is accelerated by determining whether the expression level of cryptochrome 1 is higher than the average expression level thereof in the information acquiring unit;
   outputting the determined time period by the output unit; and
   administering an anticancer drug to the cancer patient in such a manner that the administered anticancer drug reaches a liver of the cancer patient in the determined time period.

2. The method according to claim 1, wherein cisplatin is administered by intraperitoneal injection 2 hours before the determined time period within the 24 hour cycle of cryptochrome 1, wherein the expression level of cryptochrome 1 is increased to the highest amount.

3. The method according to claim 1, wherein the expression level of cryptochrome 1, is measured after forskolin treatment of the sample and synchronization of a bio-cycle of cells contained in the sample.

4. The method according to claim 1, further comprising measuring activation of Ataxia telangiectasia and Rad3 related ('ATR') by identifying the activity of at least one protein selected from phosphorylated-checkpoint kinase 1 (p-Chk1) and phosphorylated-protein 53 (p-p53).

5. The method according to claim 4, wherein the ATR activation is measured by identifying the activity of phosphorylated-minichromosome maintenance protein 2 (p-MCM2).

* * * * *